(12) United States Patent
Eskandari et al.

(10) Patent No.: US 9,679,375 B2
(45) Date of Patent: Jun. 13, 2017

(54) OVARIAN FOLLICLE SEGMENTATION IN ULTRASOUND IMAGES

(71) Applicant: Ultrasonix Medical, Richmond (CA)

(72) Inventors: Hani Eskandari, Vancouver (CA);
Reza Zahiri Azar, Vancouver (CA);
Linda Pendziwol, Nanaimo (CA)

(73) Assignee: Ultrasonix Medical Corporation, British Columbia, CA (US)

( * ) Notice: Subject to any disclaimer, the term of this patent is extended or adjusted under 35 U.S.C. 154(b) by 0 days.

(21) Appl. No.: 14/836,408

(22) Filed: Aug. 26, 2015

(65) Prior Publication Data

US 2017/0061607 A1 Mar. 2, 2017

(51) Int. Cl.
*G06K 9/00* (2006.01)
*G06T 7/00* (2017.01)
(Continued)

(52) U.S. Cl.
CPC ............ *G06T 7/0012* (2013.01); *A61B 8/08* (2013.01); *A61B 8/5269* (2013.01); *G06K 9/4604* (2013.01); *G06T 5/20* (2013.01); *G06T 5/30* (2013.01); *G06T 7/0081* (2013.01); *G06T 2207/10132* (2013.01); *G06T 2207/20192* (2013.01)

(58) Field of Classification Search
USPC ............ 382/100, 103, 128–133, 168, 173, 382/180–181, 203, 209, 199, 190, 219, 382/224, 232, 254, 274–276, 286–291, 382/298, 305, 312; 128/916, 200.16; 506/9; 435/29
See application file for complete search history.

(56) References Cited

U.S. PATENT DOCUMENTS 6,858,007 B1 * 2/2005 Akselrod ............... A61B 6/466
128/916
2008/0267499 A1 * 10/2008 Deischinger ......... G06K 9/3233
382/173
(Continued)

OTHER PUBLICATIONS

Anthony Krivanek, et al., Ovarian Ultrasound Image Analysis: Follicle Segmentation, IEEE Transactions on Medical Imaging, vol. 17, No. 6, Dec. 1998.*

(Continued)

*Primary Examiner* — Seyed Azarian
(74) *Attorney, Agent, or Firm* — Anthony M. Del Zoppo, III; Driggs, Hogg, Daugherty & Del Zoppo, Co., LPA

(57) ABSTRACT

A method includes constructing a variation image from an ovarian follicle B-mode ultrasound image, wherein the variation image is indicative of local variations in the ovarian follicle B-mode ultrasound image, constructing a binary image from the variation image and the ovarian follicle B-mode image, identifying connected components in the binary image, wherein each connected component corresponds to a different ovarian follicle candidate, constructing a coarse follicle mask from the binary image where each identified connected component represents a mask for a corresponding different ovarian follicle candidate in the binary image, optimizing contours of the follicles in the coarse follicle mask, and segmenting one or more ovarian follicles from the ovarian follicle B-mode ultrasound image with the optimized follicle mask.

18 Claims, 7 Drawing Sheets

(51) Int. Cl.
*A61B 8/08* (2006.01)
*G06T 5/20* (2006.01)
*G06T 5/30* (2006.01)
*G06K 9/46* (2006.01)
*B05B 17/06* (2006.01)

(56) References Cited

U.S. PATENT DOCUMENTS

| | | | | |
|---|---|---|---|---|
| 2010/0055730 A1* | 3/2010 | Usheva-Simidjiyska | ............... | G01N 33/6893 435/29 |
| 2012/0283125 A1* | 11/2012 | Sirard | ............... | C12Q 1/6883 506/9 |
| 2013/0231258 A1* | 9/2013 | Wilde | ............... | C12Q 1/6879 506/9 |

OTHER PUBLICATIONS

Alexandra Rolaki, et al., Novel trends in follicular development, atresia and corpus luteum regresson: a role for apoptosis, vol. 11, No. 1, 2005 93-103 Reproductive BioMedicine Online: www.rbmonline.com/Article/1754 on web Jun. 2, 2005.

Gordon E. Sarty, et al., Semiautomated segmentation of Ovarian Follicular Ultrasound Images Using a Knowledge-based Algorithm, Ultrasound in Med. & Biol., vol. 24, No. 1, pp. 22-42, 1998.

Mitja Lenic, et al., Fast Segmentation of Ovarian Ultrasound Volume Using Support Vector Machines and Sparse Learning Sets, G.A. Tsihrintzis et al. (Eds.): New Direct, in Intel. Interac. Multimedia, SCI 142, pp. 95-105, 2008.

P.S. Hiremath, et al., Fuzzy inference system for follicle detection in ultrasound images of ovaries, Methodologies and Application, Soft Comput (2014) 18:1353-1362 DOI 10.1007/s00500-013-1148-x, published online: Oct. 30, 2013 Springer-Verlag Berlin Heidelberg 2013.

Bozidar Potocnik, et al., Computerized detection and recognition of follicles in ovarian ultrasound images: a review, Med. Biol. Eng Comput (2012) 50:1201-1212 DOI 10/1007/s11517-012-0956-y, Received Jan. 20, 2012/Accepted: Sep. 13, 2012/Published online: Sep. 26, 2012.

Bart M. Ter Haar Romeny, et al.Computer Assisted Human Follicle Analysis for Fertility Prospects with 3D Ultrasound, Information Proc. in Medical Imaging, Lecture Notes in Comp. Sci., vol. 1613, pp. 56-69, 1999.

Mark J. Gooding, et al., Volume Segmentation and Reconstruction from Freehand Three-Dimensional Ultrasound Data with Application to Ovarian Follicle Measurement, Ultrasound in Med. & Biol., vol. 34, No. 2, pp. 183-195, 2008.

Terrence Chen, et al., Automatic ovarian follicle quantification from 3D ultrasound data using global/local context with database guided segmentation, 2009 IEEE 12th International Conference on Computer Vision (ICCV).

* cited by examiner

OVARIAN FOLLICLE SEGMENTATION IN ULTRASOUND IMAGES

TECHNICAL FIELD

The following generally relates to ultrasound imaging and more particular to segmenting tissue of interest such as ovarian follicles and/or other tissue of interest in ultrasound images.

BACKGROUND

Ovarian follicles are fluid-filled ovarian structures that emerge during the ovulation period. A follicle that has certain physical characteristics may contain an oocyte. To increase the chance of fertility with in vitro fertilization procedures, it is important to identify such follicles and extract the oocytes at the right time to fertilize them in vitro. Ultrasound has been used for non-invasive detection of follicles, e.g., due to its ease of use, real-time imaging, ability to delineate follicles and affordability. Follicles that are ready for extraction appear larger both in diameter and in overall area. Therefore, clinicians often use ultrasound to measure follicle diameters and manually segment them to measure their cross-sectional area as a mean to characterize individual follicles. Unfortunately, this can be a painstaking task for clinicians given that ovarian ultrasound imaging may depict as many as twenty follicles. Performing measurement on each of the individual follicles can therefore be time consuming and prone to operator errors.

Automated approaches perform automatic measurement of follicle properties in ultrasound images. One approach involves determining inner and outer walls of a follicle through cost function optimization that takes into account image intensity and directionality of the wall at each point. Unfortunately, this approach may yield non-smooth follicle borders and is sensitive to accuracy of the edge detection technique. Another approach detects an inner and an outer border of a follicle and then takes into account a distance between adjacent follicles to optimally estimate the associated outer borders. However, these approaches may lack in measurement accuracy. Generally, follicles that are 15 to 20 millimeters (mm) in diameter are considered mature and are good candidates for egg aspiration. Accurate measurement of the diameters of follicles, several of which may be visible in a single transvaginal ultrasound image, is important for precise aspiration and staging of the follicle growth.

SUMMARY

Aspects of the application address the above matters, and others.

In one aspect, a method includes constructing a variation image from an ovarian follicle B-mode ultrasound image, wherein the variation image is indicative of local variations in the ovarian follicle B-mode ultrasound image, constructing a binary image from the variation image and the ovarian follicle B-mode image, identifying connected components in the binary image, wherein each connected component corresponds to a different ovarian follicle candidate, constructing a coarse follicle mask from the binary image where each identified connected component represents a mask for a corresponding different ovarian follicle candidate in the binary image, optimizing contours of the follicles in the coarse follicle mask, and segmenting one or more ovarian follicles from the ovarian follicle B-mode ultrasound image with the optimized follicle mask.

In another aspect, an apparatus includes a follicle identifier that receives an ultrasound B-mode image generated by an ultrasound imaging system. The follicle identifier includes coarse estimator and a fine estimator. The coarse estimator is configured to employ morphological filters to identify potential ovarian follicles in the ultrasound B-mode image and determine a coarse outline of their boundaries. The fine estimator is configured to employ a non-linear optimization to refine the borders.

In another aspect, a non-transitory computer readable medium is encoded with computer executable instructions, which, when executed by a computer processor, causes the processor to: construct an entropy image with a B-mode image, low pass filter the B-mode image, construct a binary image based on pixels values of both entropy image and the low pass filtered B-mode image, morphologically filter the binary image, identify connected components in the morphologically filtered binary image, create a coarse follicle mask with the connected components having an area that satisfied a predetermined threshold, refine contours of the follicles coarse follicle mask, and identify ovarian follicle B-mode image based on the follicles with the refined contours.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

The following describes a segmentation approach to outline borders of follicles in ovarian ultrasound images.

Figure 1:
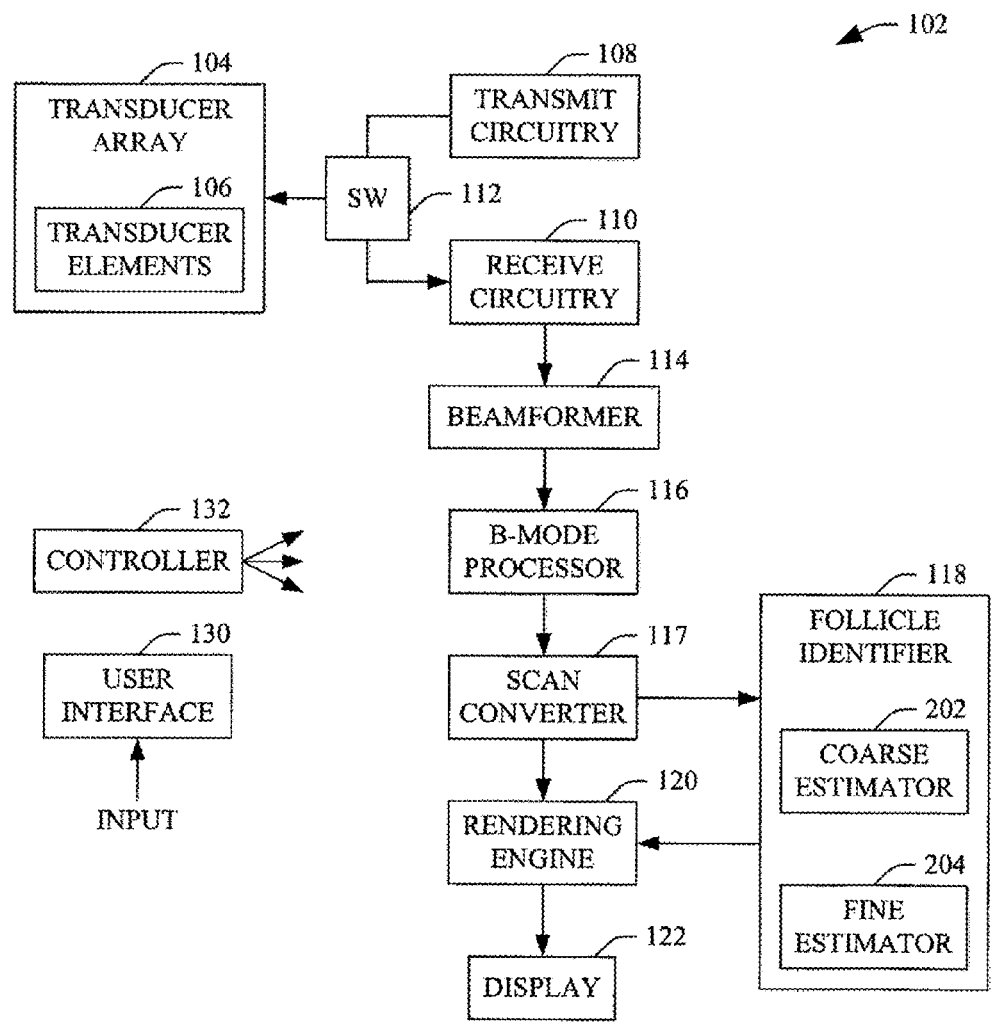
FIG. 1 schematically an example imaging system and a follicle identifier.

FIG. 1 schematically illustrates an ultrasound (US) imaging system 102. The ultrasound imaging system 102 includes a transducer array 104 with at least one transducer element 106. The at least one transducer element 106 is configured to convert electrical signals to an ultrasound pressured field and vice versa respectively to transmit ultrasound signals into a field of view and receive echo signals, generated in response to interaction with structure in the field of view, from the field of view. The transducer array 104 can be linear, curved (e.g., concave, convex, etc.), circular, etc., fully populated or sparse, etc.

Transmit circuitry 108 generates a set of pulses (or a pulsed signal) that are conveyed, via hardwire (e.g., through a cable) and/or wirelessly, to the transducer array 104. The set of pulses excites a set (i.e., a sub-set or all) of the at least one transducer element 106 to transmit ultrasound signals. Receive circuitry 110 receives a set of echoes (or echo signals) generated in response to a transmitted ultrasound signal interacting with structure in the field of view. A switch (SW) 112 controls whether the transmit circuitry 108 or the receive circuitry 110 is in electrical communication with the at least one transducer element 106 to transmit ultrasound signals or receive echoes.

A beamformer 114 processes the received echoes by applying time delays to echoes, weighting echoes, summing delayed and weighted echoes, and/or otherwise beamforming received echoes, creating beamformed data. A B-mode processor 116 processes the beamformed data and generates B-mode images, e.g., which includes a sequence of focused, coherent echo samples along focused scanlines of a scanplane. The B-mode processor 116 may also be configured to process the scanlines to lower speckle and/or improve specular reflector delineation via spatial compounding, and/or perform other processing such as FIR filtering, IIR filtering, edge enhancement, etc. A scan converter 117 scan converts the output of the B-mode processor 116 to generate data to display.

A follicle identifier 118 is configured to segment ovarian follicles from an ultrasound (e.g., B-mode) and/or other images. In general, ovarian follicles have certain characteristics, which can be seen in FIG. 2. These characteristics include the following characteristics. Follicles are circular or elliptical in shape in the form of a convex hull. The pressure from the fluid contained in fully developed or ripe follicles, which are the main subjects of ovarian ultrasound examinations, cause them to grow from all directions, thus forming a convex hull. Being a convex hull, the cross-sectional perimeter of a follicle constitutes a smooth curve.

Furthermore, follicles are anechoic regions in the image with little to no specular texture inside them. The fluid inside the follicles does not contain any scatterers and therefore does not generate any reflections due to ultrasound insonification. The variance of the echo data is small inside a follicle, so image entropy tends to be small in the interior region. The wall of a follicle is at the boundary of the anechoic and isoechoic regions. Because of the lack of scatterers inside of a follicle and the presence of them in the follicular wall and the ovarian tissue surrounding the follicle, the wall can be located by finding the transition from the anechoic to the isoechoic region.

As described in greater detail below, the follicle identifier 118, through a coarse estimator 202 and a fine estimator 204, processes the B-mode image and identifies follicles and approximates their boundaries and refines the boundaries with the approximated boundaries. In one instance, this can be considered a two-stage process, wherein in a first stage the coarse estimator 202 employs morphological filters to identify follicles and find a coarse outline of their boundaries and in a second stage the fine estimator 204 employs an optimization algorithm to outline the boundaries with high accuracy. The resulting follicle mask is then used to segment follicles in the B-mod image.

The approach described herein is well-suited for ovarian follicle segmentation application as it provides an accurate delineation of follicles, which leads to more accurate identification of follicle boundaries and measurement of their diameters, which is important for precise aspiration and staging of the follicle growth. Furthermore, the process is automated and/or semi-automated such that the identification of follicle boundaries and measurement of their diameters is not a painstaking or time consuming task for clinicians and/or is less prone to human error.

The follicle identifier 118 and/or other components of the system 102 can be implemented via one or more computer processors (e.g., a central processing unit (CPU), a microprocessor, etc.) executing one or more computer executable instructions embedded or encoded on computer readable storage medium, which excludes transitory medium, such as physical memory. However, at least one of the computer executable instructions can alternatively be carried out by a carrier wave, signal, and other transitory medium and implemented via the one or more computer processors.

A rendering engine 120 visually presents the B-mode image and/or the processed B-mode image with the refined approximate follicle boundaries via a display 122. The display 122 can be a light emitting diode (LED), liquid crystal display (LCD), and/or type of display, which is part of the ultrasound imaging system 100 or in electrical communication therewith via a cable. The B-mode image and/or the processed the B-mode image can be stored locally and/or in a remote repository (e.g., a PACS).

A user interface (UI) 130 includes an input device(s) (e.g., a physical button, a touch screen, etc.) and/or an output device(s) (e.g., a touch screen, a display, etc.), which allow for interaction between a user and the ultrasound imaging system 102. A controller 132 controls one or more of the components 108-130 of the ultrasound imaging system 102. Such control includes controlling one or more of these components to perform the functions described herein and/or other functions.

In the illustrated example, the follicle identifier 118 is part of the ultrasound imaging system 102. In another embodiment, the follicle identifier 118 is separate and distinct therefrom. For example, the follicle identifier 118 can be part of another computing system, distributed across computing system, a resource of cloud based computing, etc. As such, the follicle identifier 118 may communicate with the ultrasound imaging system 102 and/or remote repository via a network (e.g., wireless communication or physical wire), a bus, etc.

As briefly discussed above, the follicle identifier 118, through the coarse estimator 202 and the fine estimator 204, processes the B-mode image and identifies follicles and approximates their boundaries and refines the boundaries with the approximated boundaries. The following describes non-limiting examples of the coarse estimator 202 and the fine estimator 204. The input to the follicle identifier 118 is a B-mode image. The B-mode image can be obtained from the ultrasound imaging system 102, another ultrasound imaging system, a data repository (e.g., a PACS), and/or other storage and/or source.

The coarse estimator 202 generates a coarse estimation of the regions in the B-mode image that contains follicles and outputs a coarse follicle mask that delineates the approximate borders of the possible follicles in the image. For this, the coarse estimator 202 processes the B-mode image to construct at least a variation image and, optionally, a pre-processed B-mode image, and then constructs the coarse follicle mask based on the variation image and either the B-mode or the preprocessed B-mode image. The variation image, in general, is representative of local variations in the image data. Examples of such images are a variance image, an entropy image, and the like. Examples of pre-processing include low pass filtering, speckle removal, and/or other pre-processing.

The following provides a non-limiting example of constructing the binary image. In this example, the coarse estimator 202 constructs the binary image by applying a predetermined threshold on the B-mode or pre-processed B-mode image and the entropy image. Any pixel with a B-mode intensity of less than $I_{th}$ and an entropy value of less than $E_{th}$ is set to one (1) in the binary image, while all the other pixels in the binary image are set to zero. Suitable values of $I_{th}$ and $E_{th}$ are 0.5-20% and 1-40% of the maximum values of the B-mode image and entropy image, respectively. For example, in one instance, 2% and 25% represent suitable values.

The following provides a non-limiting example of constructing the entropy image. In this example, entropy is a local measure of an amount of information contained locally within the B-mode image. In general, a region of an image which is locally flat with no pixel intensity variations would result in a local entropy value of zero, while large variations of pixel intensity in a local area of an image would indicate high entropy value in that area. The entropy map of a gray scale image (B-mode image in this example) is an image of the same size consisting of the entropy values for all neighborhoods of size $n_e \times m_e$ within the original gray scale image, where n and m are positive integers.

In one instance, the entropy of a dataset of size $n_e \times m_e$ is determined by first computing a probability of each gray scale intensity value in the data set. Intensity probabilities can be computed using histogram of the data with a certain number of histogram bins. If the histogram is computed with a total of $b_h$ bins and the $k^{th}$ bin contains $N_k$ entries, the probability of the intensity values represented by bin k would be $p_k = N_k/b_h$, and the entropy of the dataset can be computed as shown in EQUATION 1:

$$E = -\sum_{k=1}^{n_e m_e} p_k \log(p_k).\qquad \text{EQUATION 1}$$

An entropy image is constructed by computing the entropy of all the $n_e \times m_e$ neighborhoods in the gray scale image.

The binary image may contain several disconnected pixels of the same value. For example, background pixels with value zero may contain random instances of pixels with a value of one, and foreground pixels that have a value of one and indicate potential follicles may contain random and disconnected pixels with a value of zero. Optionally, the coarse estimator 202 can remove instances of random ones in the background by applying a morphological opening operator on the binary image and/or remove instances of random zeroes in the foreground by applying a morphological closing operator on the binary image. Alternative optional processing to remove this unwanted image noise includes dilation, erosion, etc.

The coarse estimator 202 identifies connected regions within the binary image and labels each of them as an individual follicle masks. The resulting masks may contain non-convex hull shapes. Optionally, in order to make the follicle masks to look more like a convex hull, the coarse estimator 202 morphologically filters or opens the mask for each follicle with a kernel. The kernel can be rectangular, circular, elliptical or any other shape and its cross-sectional area must be smaller than the cross sectional area of a typical follicle. Optionally, the cross-sectional area of the kernel can be on an order of one tenth of the area of a follicle in the image. If the original follicle mask is a convex hull, this operation should not change the overall area; otherwise, the follicle may divide into two or more follicles and their cumulative areas would be different than that of the original follicle.

Where morphological filters are employed, the coarse estimator 202 compares each original connected region with its corresponding morphologically filtered connected region. If a change in the area between the two is greater than a predetermined threshold, the coarse estimator 202 determines this is a significant change which would re-define the follicle candidates. In this instance, the coarse estimator 202 performs another round of morphological opening of the connected components and comparing areas with the previous connected components to determine the change. An example of a threshold is more than 3.00%, 4.50%, 5.00%, 6.25%, 10.00%, or other percent, which may be greater or less.

The coarse estimator 202 then thresholds the size of the opened connected regions to extract those large-enough to be considered candidates and/or discard those too small to be considered candidates. A reasonable threshold is 20 mm$^2$, indicating that follicles only larger than 5 mm in diameter are deemed potential candidates. Any other value for area threshold and diameter threshold based on clinical evaluation of follicles in in vitro fertilization can be acceptable. The result provides an approximate estimate of the follicles in a coarse follicle mask.

The coarse estimator 202 can identify a dominate follicle in the image based on the estimate of the follicles. This can be an automated process (with no human interaction) and/or semi-automated with human interaction in that a user can manually indicate any region that has the characteristics of a follicle, but has not been segmented in the fully-automated technique. In the semi-automated follicle segmentation technique, a user indicates a point that lies within the follicle of interest. Then, the candidate follicle is automatically segmented and its border is reconstructed. If the point that has been indicated by the user falls within an area designated as potential follicle in the binary image, then the connected pixels within the binary image will be selected and further dilated to perform border optimization. If the indicated initial point does not fall within a viable mask area, then the point will be ignored.

Figure 2:
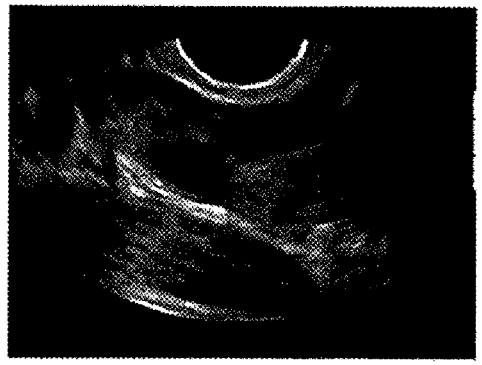
FIG. 2 depicts an original B-mode image.
Figure 3:
FIG. 3 depicts an entropy image.
Figure 4:
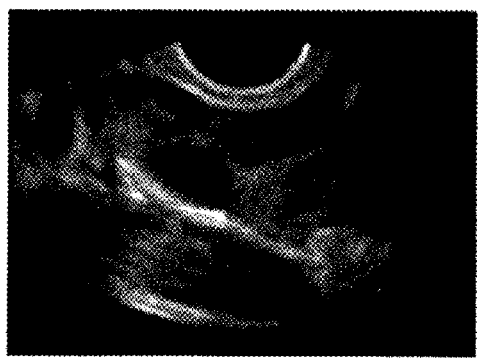
FIG. 4 depicts a low pass filtered B-mode image.
Figure 5:
FIG. 5 depicts a binary image constructed with the entropy and filtered images.
Figure 6:
FIG. 6 depicts the binary image after removing noise.
Figure 7:
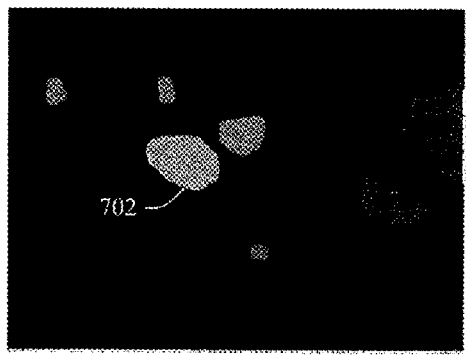
FIG. 7 depicts a coarse follicle estimate image.

FIGS. 2, 3, 4, 5, 6 and 7 illustrate an example of the above. FIG. 2 shows the original B-mode image. FIG. 3 shows an entropy image. FIG. 4 shows a filtered B-mode image, where the filtering operation is applied. FIG. 5 shows a binary image constructed with the entropy and filtered images. FIG. 6 shows binary image after removing noise. FIG. 7 shows the connected components after the additional opening and dilation operations. In FIG. 7, a follicle 702 is identified as the dominate follicle.

The fine estimator 204 optimizes the contour of a follicle wall of each follicle in the coarse follicle mask. In the following example, the fine estimator 204 employs a non-linear optimization that maximizes a diameter of a follicle while keeping the cumulative echo intensity inside it at a minimum. In other embodiments, other optimization approaches can be employed.

Figure 8:
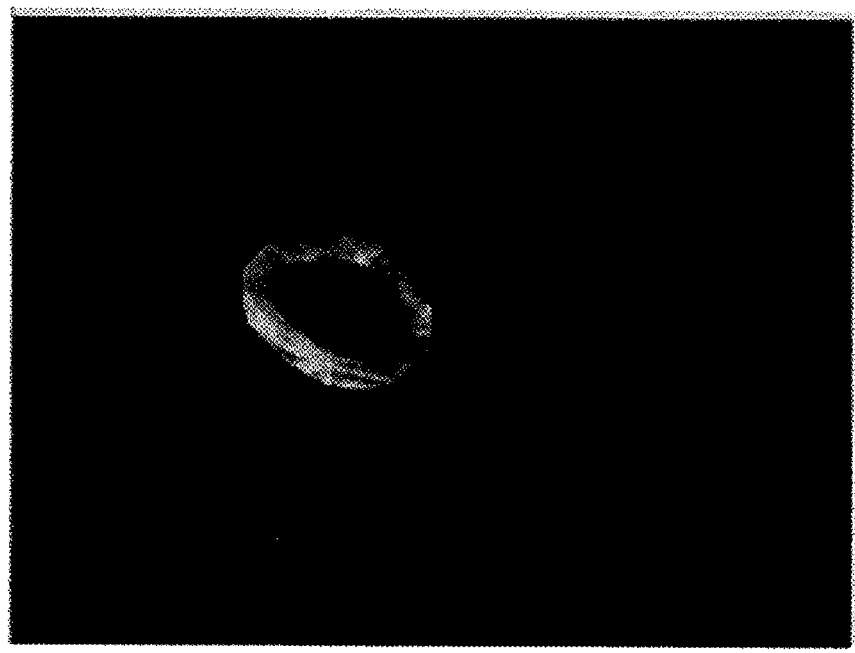
FIG. 8 depicts a Cartesian representation of a follicle of FIG. 7.
Figure 9:
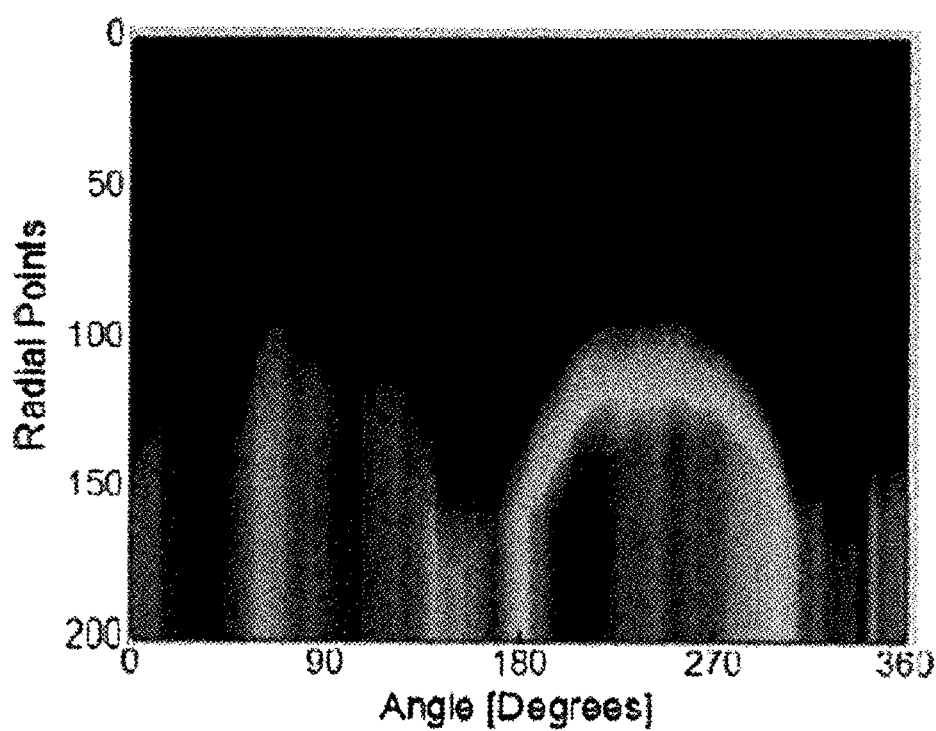
FIG. 9 depicts a polar representation of the follicle of FIG. 8.

The fine estimator 204 first maps every follicle detected from the coarse estimation to the polar coordinate system taking its center of mass as the origin. For this, the gray scale B-mode image is multiplied by the dilated mask of the follicle discussed above, yielding only the follicle of interest in the Cartesian coordinate system. A center of mass of the follicle mask is also calculated and assumed to be the origin and then the polar map of the follicle is constructed using pre-specified angular and radial resolutions. FIGS. 8 and 9 respectively show Cartesian and polar representations of the follicle 702 of FIG. 7. In FIG. 9, the last value at a given angle is used for the radial points that are beyond the extent of the Cartesian mask. As a consequence, the polar image appears to be washed out vertically after a certain radial point at each angle.

In one non-limiting example, an angular resolution is set to 0.5 degree, which corresponds to 720 angular points. Also, the radial discretization is set to 200 points, yielding sub-pixel resolution even for large follicles in standard B-mode images. These settings result in a fixed-size polar image, while maintaining sufficient accuracy for the optimization result. Other angular resolution and/or radial discretization values are also contemplated herein. For example, the radial discretization can be set to achieve a consistent optimization resolution, at the cost of having different computation times for different follicles.

The conversion of the Cartesian representation of a particular follicle to the polar representation is performed to the smallest rectangular window that contains the follicle mask as obtained in the coarse estimation. The angle measurements are performed in standard trigonometric position, with the angle increasing in the counter clock-wise direction. To further improve the estimates of follicle borders, a morphological dilation operator is first applied to each binary follicle mask to ensure that the mask would cover a region large enough to encompass the follicle wall, and next a non-linear optimization problem is solved for each of the follicles found in the morphological processing.

The fine estimator 204 optimizes the contour of a follicle wall by finding the optimal curve in the polar representation of each follicle such that a predetermined set of follicle characteristics (e.g., such as one or more of those described herein) are satisfied. Such a curve should appear as a functional graph in the angular-radial plane, meaning that each angular point should corresponds to one and only one radial point on the curve. In one non-limiting example, the optimization is formulated by defining a following cost function.

EQUATION 2 shows an example suitable cost function.

$$P(\theta) = \arg\max_{p} \sum_{i=1}^{n_f} \sum_{k=1}^{n_a} \alpha_i f_i(p(\theta_k))^2, \quad \text{EQUATION 2}$$

where, $$\theta_k = 2\pi \frac{(k-1)}{n_a}, \text{ and}$$

$$0 \le p(\theta_k) \le r_{n_r}.$$

where $\theta_k$ is a $k^{th}$ angular step out of a total $n_a$, $p(\theta)$ is an optimal curve function with each value representing a radius of the follicle at every angle, $n_r$ is a number of radial points used in the radial discretization, and $r_{n_r}$ is a maximum possible radius of the follicle.

EQUATION 2 combines $n_f$ different functionals, $f_i(\bullet)$, each introducing a penalty on the curve. The contribution of each functional in the overall cost function is determined scalar weights alpha$_i$. Without loss of generality and in order to normalize the cost function, alpha$_0$ can be set to 1. The objective of the optimization process is to find the optimal curve such that the EQUATION 2 is minimized With $p_0(\theta)$ being the initial guess of the optimal curve and Z being the polar image of the follicle, the following are a non-limiting set of suitable functionals:

$$f_0(p(\theta)) = Z(p(\theta), \theta),$$

$$f_1(p(\theta)) = \frac{1}{p(\theta) - p_0(\theta) + 1},$$

$$f_2(p(\theta)) = \frac{\partial p(\theta)}{\partial \theta}, \text{ and}$$

$$f_3(p(\theta)) = \frac{\partial^2 p(\theta)}{\partial \theta^2},$$

where $Z(p(\theta), \theta)$ is the polar image sampled at the coordinates of the optimal curve. Each of $f_0$, $f_1$, $f_2$ and $f_3$ measure a certain feature in the follicle characteristics. $f_0$ enforces lower image intensity on the follicle borders, $f_1$ is small as the cumulative diameter of the follicle is large, $f_2$ and $f_3$ penalize the first and second derivatives of the curve function, enforcing a smooth border for individual follicles.

Solving for the optimal curve in EQUATION 2 includes the use of a nonlinear optimization technique. An example of suitable optimization techniques are discussed in J. Nocedal, S. Wright, Numerical Optimization, 2nd Edition, Springer, 2006. For example, a suitable optimization technique is an iterative approach for non-linear least-squares optimization such as the Levenberg-Marquardt (LM) optimization, which is a combination of Newtons and steepest decent algorithms. With this approach, at each iteration, a step direction is computed which would guide the cost function to a local minimum.

The initial guess, $p_0(\theta)$, is chosen to be, at every angle, the smallest radial point at which the underlying polar image is larger than the $I_{th}$ threshold. At every iteration, i, a step direction is computed as $\Delta p_i(\theta)$ and the curve is updated as shown in EQUATION 3:

$$p_i(\theta) = p_{i-1}(\theta) + c_i \Delta p_i(\theta) \quad \text{EQUATION 3}$$

where $p_i(\theta)$ is the curve function at iteration i and $c_i$ is the step size.

In the Newtons and LM methods, the step direction is computed by calculating the Jacobian matrix of the cost function as follows as shown in EQUATION 4:

$$J^T = \left[\frac{\partial f}{\partial p}\right]^T = \left[\left[\frac{\partial f_0}{\partial p}\right]^T \left[\frac{\partial f_1}{\partial p}\right]^T \left[\frac{\partial f_2}{\partial p}\right]^T \left[\frac{\partial f_3}{\partial p}\right]^T\right], \quad \text{EQUATION 4}$$

where $[\bullet]^T$ is the transpose operator, According to Newtons algorithm, the optimal descent can be computed as shown in EQUATION 5:

$$J^T W J \Delta p(\theta) = -J^T W f, \quad \text{EQUATION 5}$$

where, $$W = \begin{bmatrix} I & 0 & 0 & 0 \\ 0 & \alpha_1 I & 0 & 0 \\ 0 & 0 & \alpha_2 I & 0 \\ 0 & 0 & 0 & \alpha_3 I \end{bmatrix},$$

where I is the identity matrix. According to the LM method, the Newtons step can be modified to address situations where the Hessian matrix $J^T W J$ is not positive definite (i.e. the Hessian matrix has such small eigenvalues that make its inversion infeasible). The Tikhonov regularization, whereby a small perturbation, $\lambda I$, is added to the Hessian, guarantees positive definiteness. The result is shown in EQUATION 6:

$$(J^T W J + \lambda I)\Delta p(\theta) = -J^T W f. \quad \text{EQUATION 6}$$

In one instance, the regularization is used only as a preventative measure to avoid unexpected behavior of the optimization process. Examples values of $\lambda$ are $10^{-20}$-10. Small values such as $10^{-12}$ ensure the convergence speed of the Newtons method would be attained while ensuring convergence stability of the LM algorithm. Furthermore, since the regularization is small and the solution method is similar to the Newtons algorithm, the step size has been set equal to the optimal step size of the Newtons method, i.e. $c_i=1$.

Figure 10:
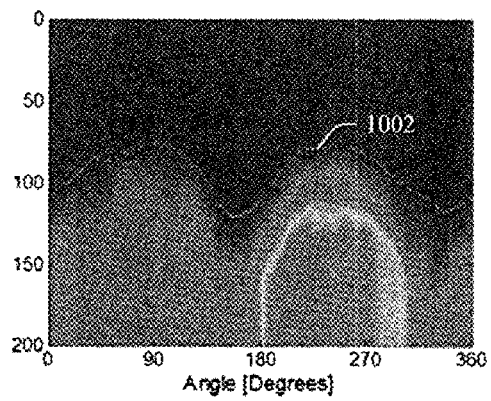
FIG. 10 shows an initial guess of a follicle border superimposed on a polar map.
Figure 11:
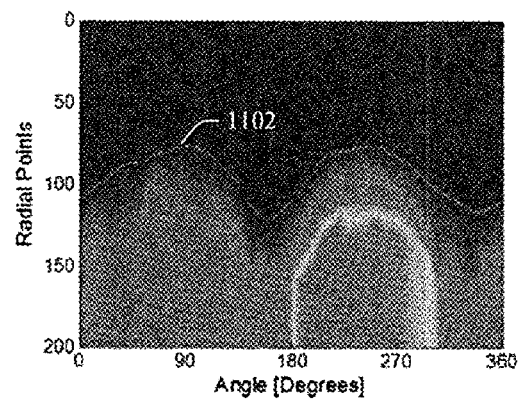
FIG. 11 shows the border of FIG. 10 after several optimization iterations.
Figure 12:
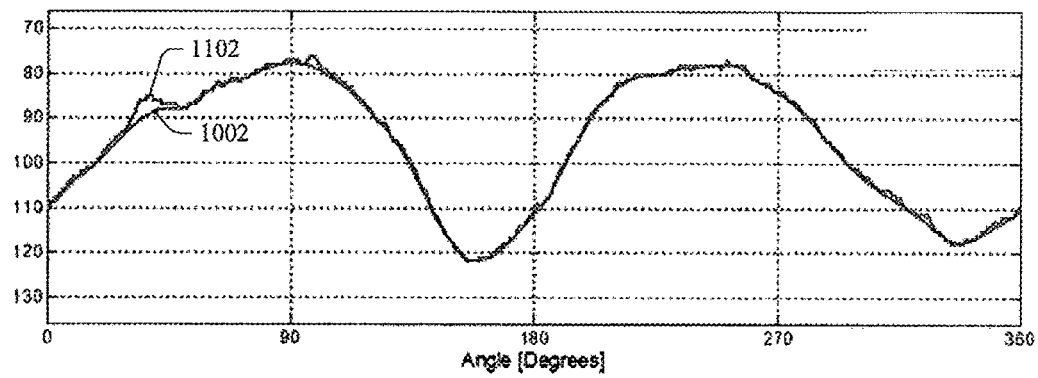
FIG. 12 show the curves of FIGS. 10 and 11 plotted in one view.
Figure 13:
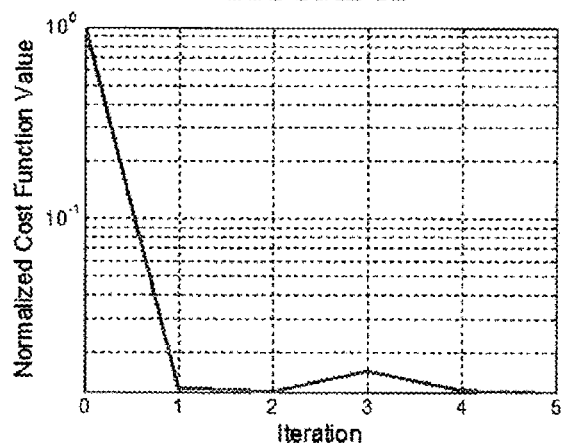
FIG. 13 shows values of a cost function at different iterations.
Figure 14:
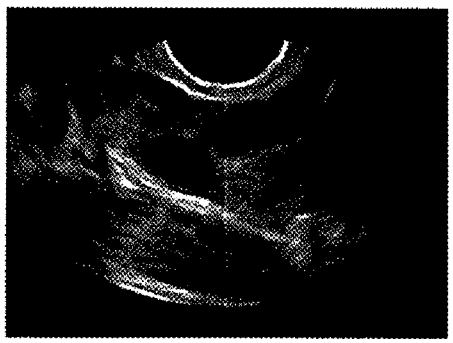
FIGS. 14 and 15 respectively depict a first example with an original B-mode image and a corresponding segmented B-mode image with identified follicles.
Figure 15:
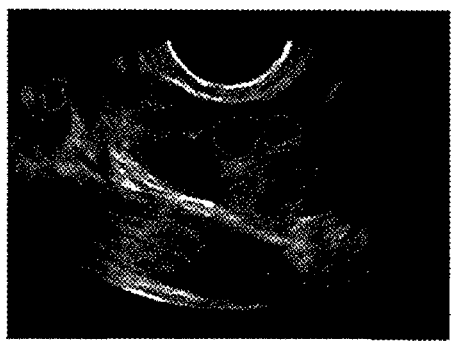
Figure 16:
FIGS. 16 and 17 respectively depict a second example with an original B-mode image and a corresponding segmented B-mode image with identified follicles.
Figure 17:
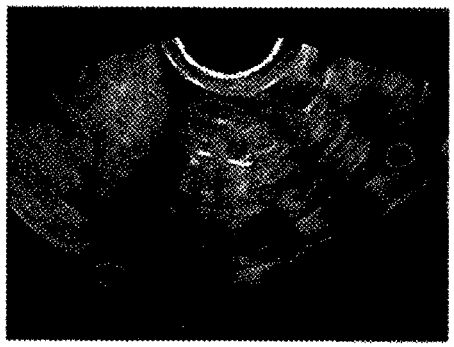
Figure 18:
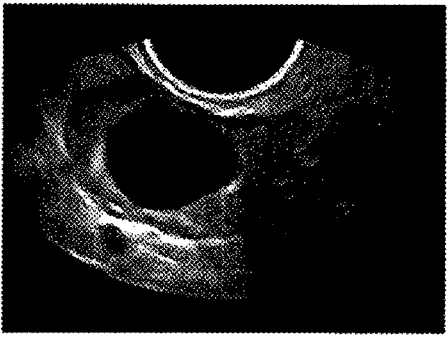
FIGS. 18 and 19 respectively depict a third example with an original B-mode image and a corresponding segmented B-mode image with identified follicles.
Figure 19:
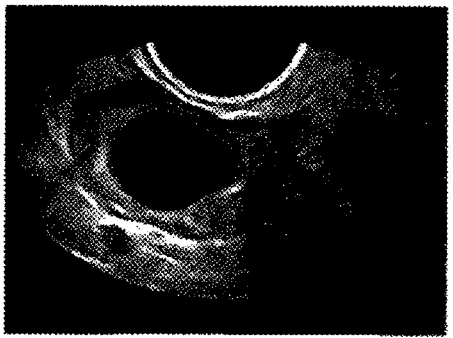
Figure 20:
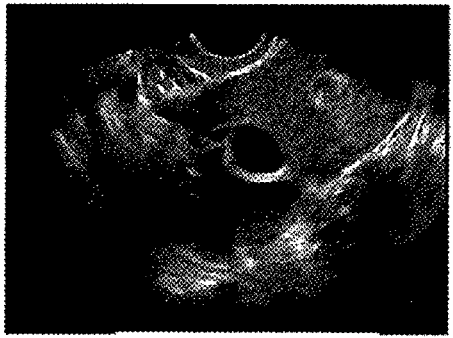
FIGS. 20 and 21 respectively depict a fourth example with an original B-mode image and a corresponding segmented B-mode image with identified follicles.
Figure 21:

For the follicle shown in FIG. 8, the initial curve 1002 and a curve 1102 obtained after five iterations are depicted in FIGS. 10 and 11, respectively. FIG. 10 shows the initial guess of the border superimposed on the polar map of the follicle, and FIG. 11 shows the 5th iteration. To illustrate the enhancement that was achieved, the two curves are plotted in a larger and expanded view in one view in FIG. 12. In this example, $\alpha_1=10^3$, $\alpha_2=5\times10^4$ and $\alpha_3=10^5$. The values obtained for the cost function at each iteration using EQUATION 2 are normalized with respect to the value of the cost function evaluated with the initial curve and plotted in FIG. 13, which shows values of the cost function at different iterations normalized to the value at initial iteration.

FIGS. 14, 15, 16, 17, 18, 19, 20 and 21 show a few examples of the results after applying the above. FIGS. 14, 16, 18 and 20 show original B-mode images, and FIGS. 15, 17, 19 and 21 show corresponding segmented B-mode images identified follicles. A few follicles have been identified on the boundaries of the images in FIGS. 17 and 19. Generally such follicles are not of interest to the clinician since the most important follicles are placed in the middle of the image prior to performing automated segmentation. These follicles can be remove or not shown in the first place. In FIGS. 15, 17, 19 and 21, no area threshold is applied so that all follicle candidates are illustrated. In a clinical setting, applying such a threshold will remove unwanted follicles based on the preference of the clinician.

Changing the settings on the parameters in EQUATION 2 may result in different segmentation result. The identified follicles may remain the same, however, their diameter and border smoothness will change based on how the operator would prefer to see the region segmented. Since the optimization problem requires solving several iterations of large systems of equations for every follicle, this approach can be computationally intensive. In general, the first step of obtaining a coarse estimate of the follicle borders is significantly faster than the iterative optimization procedure.

Generally, with this approach, in the first stage the approximate boundary of one or more follicles is detected. In the second stage, for each follicle, using the result from the first stage as a priori data, an optimization problem is solved to find the most likely boundary map for the follicle. While the first stage segmentation relies on morphological image filtering using image intensity maps and entropy, the second stage takes the smoothness of the follicle boundary contour into account while minimizing a cost function. With the approach described herein, accurate measurements of the follicles can be made, which allows for precise aspiration and staging of the follicle growth.

Figure 22:
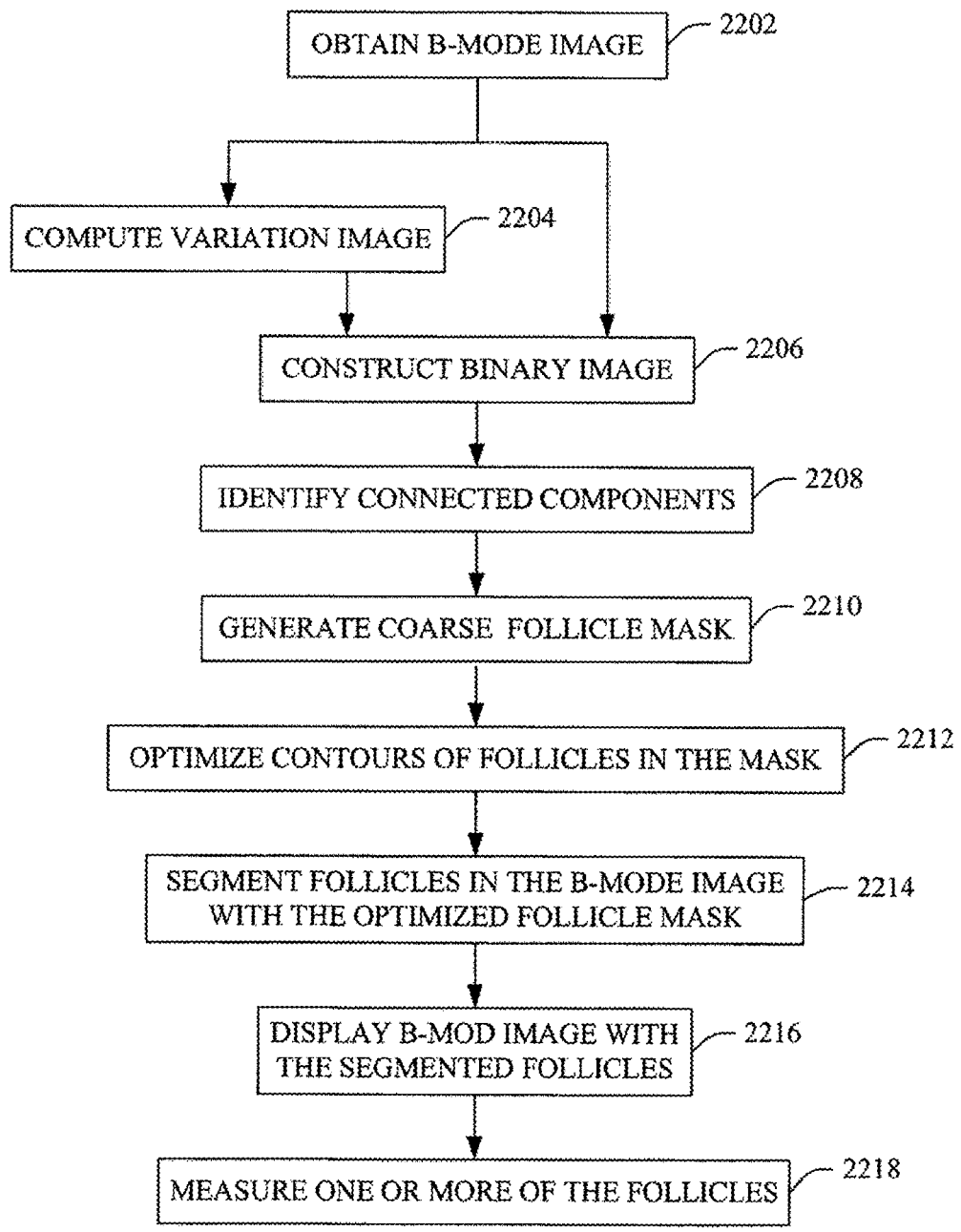
FIG. 22 illustrates an example method in accordance with an embodiment herein.

FIG. 22 illustrates an example method in accordance with an embodiment herein.

It is to be appreciated that the ordering of the above acts is not limiting. As such, other orderings are contemplated herein. In addition, one or more acts may be omitted and/or one or more additional acts may be included.

At 2202, a B-mode of ovarian follicles is obtained, as described herein and/or otherwise.

At 2204, a variation image is constructed from the B-mode, as described herein and/or otherwise.

At 2206, a binary image is constructed from the variation image and the B-mode using a predetermined threshold, as described herein and/or otherwise.

At 2208, connected components are identified in the binary image, as described herein and/or otherwise.

At 2210, a coarse follicle mask is generated based on the connected components, as described herein and/or otherwise.

At 2212, contours of the connected components are optimized in the coarse follicle mask, as described herein and/or otherwise.

At 2214, follicles in the B-mode image are segmented with the optimized follicle mask.

At 2216, the B-mode image with the segmented follicles is displayed.

At 2218, one or more of the segmented follicles are measured.

Figure 23:
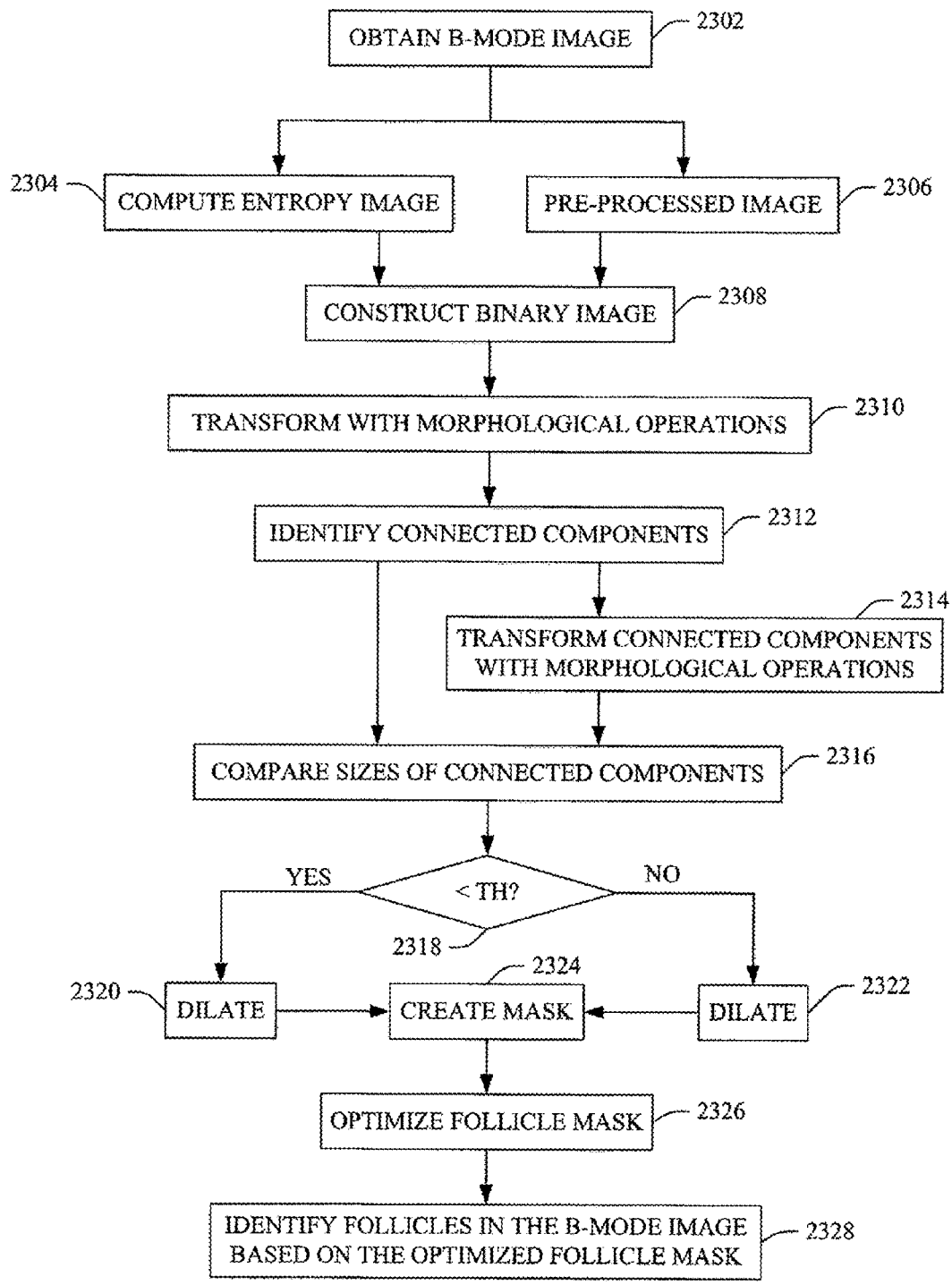
FIG. 23 illustrates another example method in accordance with an embodiment herein.

FIG. 23 illustrates another example method in accordance with an embodiment herein.

It is to be appreciated that the ordering of the above acts is not limiting. As such, other orderings are contemplated herein. In addition, one or more acts may be omitted and/or one or more additional acts may be included.

At 2302, a B-mode of ovarian follicles is obtained, as described herein and/or otherwise.

At 2304, a variation image is constructed from the B-mode, as described herein and/or otherwise.

At 2306, the B-mode image is pre-processed, producing a pre-processed image, as described herein and/or otherwise.

At 2308, a binary image is constructed from the variation image and the B-mode using a predetermined threshold, as described herein and/or otherwise.

At 2310, the binary image is morphologically filtered, as described herein and/or otherwise.

At 2312, connected components are identified in the morphologically processed binary image, as described herein and/or otherwise.

At 2314, each connected component is morphologically filtered, as described herein and/or otherwise.

At 2316, a size of the original and morphologically filtered connected components is compared, as described herein and/or otherwise.

At 2318, if a difference for a connected component is less than a predetermined threshold (TH), at 2320 the connected component is processed with a first dilation algorithm; Otherwise, at 2322 the connected component is processed with a second dilation algorithm.

At 2324, the dilated connected components are thresholded with a predetermined threshold, where only connected components greater than (or equal to and greater than) the threshold are identified to create a coarse follicle mask of candidate follicles, as described herein and/or otherwise.

At 2326, contours of the candidates are optimized, as described herein and/or otherwise.

At 2328, a follicle in the B-mode image is identified based on the optimized follicle mask, as described herein and/or otherwise.

At least a portion of the methods discussed herein may be implemented by way of computer readable instructions, encoded or embedded on computer readable storage medium (which excludes transitory medium), which, when executed by a computer processor(s), causes the processor(s) to carry out the described acts. Additionally or alternatively, at least one of the computer readable instructions is carried by a signal, carrier wave or other transitory medium.

Although the above is described in the context of ovarian follicles, it is to be understood that other tissue and/or objects with similar characteristics as those described herein are also contemplated herein.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
   constructing a variation image from an ovarian follicle B-mode ultrasound image, wherein the variation image is indicative of local variations in the ovarian follicle B-mode ultrasound image, and wherein the variation image includes one of a variance image and an entropy image;
   constructing a binary image from the variation image and the ovarian follicle B-mode image;
   identifying connected components in the binary image, wherein each connected component corresponds to a different ovarian follicle candidate;
   constructing a coarse follicle mask from the binary image where each identified connected component represents a mask for a corresponding different ovarian follicle candidate in the binary image;
   optimizing contours of the follicles in the coarse follicle mask; and
   segmenting one or more ovarian follicles from the ovarian follicle B-mode ultrasound image with the optimized follicle mask.

2. The method of claim 1, wherein constructing the binary image includes:
   setting a value of a pixel in the binary image to a value of one only if a first corresponding pixel in the variation image is less than a first predetermined threshold and a second corresponding pixel in the ovarian follicle B-mode ultrasound image is less than a second predetermined threshold.

3. The method of claim 1, further comprising: pre-processing the ovarian follicle B-mode ultrasound image, constructing a pre-processed image, wherein the pre-processing includes at least one of low pass filtering the ovarian follicle B-mode ultrasound image and removing speckle from the ovarian follicle B-mode ultrasound image.

4. The method of claim 3, wherein constructing the binary image includes:
   setting a value of a pixel in the binary image to a value of one only if a first corresponding pixel in the variation image is less than a first predetermined threshold and a second corresponding pixel in the pre-processed image is less than a second predetermined threshold.

5. The method of claim 1, wherein the binary image includes noise, wherein the noise includes at least one of a pixel with a value of one in a region of pixels with values of zero and a pixel with a value of zero in a region of pixels with values of one, and further comprising: processing the binary image to remove the noise.

6. The method of claim 5, wherein the binary image is processed with at least one of morphological opening and closing operations, dilation and erosion.

7. The method of claim 1, further comprising:
   extracting only identified connected components having an area that satisfies a predetermined follicle size threshold; and
   constructing the coarse follicle mask with the extracted connected components.

8. The method of claim 1, wherein the binary image includes at least one connected component that has a non-convex hull shape, and further comprising: morphologically filtering the connected component which re-shapes the at least one connected component so that it has convex hull shape.

9. The method of claim 8, wherein the morphologically filtering employs a disk-shaped kernel with an area on an order of one tenth of the area of the connected component.

10. The method of claim 8, further comprising:
    comparing an area of a morphologically filtered connected component with an area of a corresponding connected component;
    dilating the connected component with a first scaling factor in response to a difference in the areas satisfying a predetermined threshold; and
    dilating the connected component with a second scaling factor in response to a difference in the areas not satisfying the predetermined threshold.

11. The method of claim 8, further comprising:
    extracting only dilated connected components having an area that satisfies a predetermined follicle size threshold; and
    constructing the coarse follicle mask with the extracted connected components.

12. The method of claim 1, wherein follicle walls are optimized by finding an optimal curve in a polar representation of each follicle such that a predetermined set of follicle characteristics are satisfied.

13. The method of claim 12, wherein the optimizing includes:
    multiplying the ovarian follicle B-mode image by a follicle mask, producing only the follicle in a Cartesian coordinate system;
    calculating a center of mass of the follicle mask;

constructing a polar map of the follicle using pre-specified angular and radial resolutions; and optimizing the contour by minimizing a cost function.

14. An apparatus, comprising:
a follicle identifier that receives an ultrasound B-mode image generated by an ultrasound imaging system, wherein the follicle identifier includes:
   a coarse estimator configured to employ morphological filters to identify potential ovarian follicles in the ultrasound B-mode image and determine a coarse outline of their boundaries, wherein the course estimator constructs a variance image or an entropy image from the ultrasound B-mode image, constructs a binary image from the variance or entropy image and the ultrasound B-mode image or a pre-processed ultrasound B-mode image, identifies candidate ovarian follicle in the binary image through connected components, and constructs a course follicle mask which includes the coarse outline of the boundaries, where each identified connected component represents a mask for a corresponding different ovarian follicle candidate in the binary image; and
   a fine estimator configured to employ a non-linear optimization to refine the borders.

15. The apparatus of claim 14, wherein the coarse estimator identifies, automatically or semi-automatically, a dominate follicle in the coarse follicle mask, and further comprises: displaying the coarse follicle mask with indicia highlighting the dominate follicle.

16. The apparatus of claim 14, wherein the coarse estimator morphologically opens and closes the binary image generating a de-noised binary image, and morphologically filters the candidate ovarian follicles to re-shape candidate ovarian follicles not satisfying a predetermined follicle shape.

17. The apparatus of claim 14, wherein the fine estimator multiplies the ultrasound B-mode image by a follicle mask producing only the follicle in a Cartesian coordinate system, calculates a center of mass of the follicle mask, constructs a polar map of the follicle using pre-specified angular and radial resolutions, and optimizes the contour through minimizing a cost function based on the polar map.

18. A non-transitory computer readable medium encoded with computer executable instructions, which, when executed by a computer processor, causes the processor to:
construct an entropy image with a B-mode image;
low pass filter the B-mode image;
construct a binary image based on pixels values of both entropy image and the low pass filtered B-mode image;
morphologically filter the binary image;
identify connected components in the morphologically filtered binary image;
create a coarse follicle mask with the connected components having an area that satisfied a predetermined threshold;
refine contours of the follicles in the coarse follicle mask; and
identify ovarian follicle B-mode image based on the follicles with the refined contours.

\* \* \* \* \*